(12) United States Patent
Oberneder et al.

(10) Patent No.: US 6,218,498 B1
(45) Date of Patent: Apr. 17, 2001

(54) ORGANOSILICON COMPOUNDS HAVING UREA GROUPS, METHOD FOR PRODUCING SAME AND THEIR UTILIZATION

(75) Inventors: Stefan Oberneder; Wolfgang Hechtl, both of Burghausen; Erich Pilzweger, Julbach; Doris Filusch; Michael Stepp, both of Burghausen, all of (DE)

(73) Assignee: Wacker-Chemie GmbH, München (DE)

( * ) Notice: Subject to any disclaimer, the term of this patent is extended or adjusted under 35 U.S.C. 154(b) by 0 days.

(21) Appl. No.: 09/308,733

(22) PCT Filed: Dec. 18, 1997

(86) PCT No.: PCT/EP97/07107

§ 371 Date: May 24, 1999

§ 102(e) Date: May 24, 1999

(87) PCT Pub. No.: WO98/29418

PCT Pub. Date: Dec. 18, 1997

(30) Foreign Application Priority Data

Dec. 27, 1996 (DE) .............................. 196 54 556

(51) Int. Cl.[7] ................................................. C08G 77/26
(52) U.S. Cl. ............................................. 528/34; 556/411
(58) Field of Search .............................. 556/411; 528/34, 528/28

(56) References Cited

U.S. PATENT DOCUMENTS

| | | |
|---|---|---|
| 3,239,489 | 3/1966 | Fink . |
| 3,337,510 | * 8/1967 | Klebe .................... 556/441 |
| 3,397,220 | * 8/1968 | Klebe .................... 556/441 |
| 3,992,428 | 11/1976 | Müller et al. . |
| 4,060,536 | 11/1977 | Kötzsch et al. . |
| 4,147,855 | 4/1979 | Schiller et al. . |
| 4,152,315 | 5/1979 | Lee et al. . |
| 4,517,337 | 5/1985 | Lockhart et al. . |
| 4,801,673 | 1/1989 | Bosch et al. . |
| 4,942,211 | 7/1990 | Sommer et al. . |
| 4,959,407 | 9/1990 | Rich et al. . |
| 5,473,037 | 12/1995 | Itoh et al. . |

FOREIGN PATENT DOCUMENTS

| | | |
|---|---|---|
| 25 07 882 | 9/1976 | (DE) . |
| 25 53 932 | 6/1977 | (DE) . |
| 27 57 936 | 9/1978 | (DE) . |
| 26 53 499 | 5/1980 | (DE) . |
| 29 53 680 C2 | 12/1983 | (DE) . |
| 36 24 206 C1 | 2/1988 | (DE) . |
| 38 01 389 A1 | 7/1989 | (DE) . |
| 0 484 959 A2 | 5/1992 | (EP) . |
| 1 578 183 | 11/1980 | (GB) . |

OTHER PUBLICATIONS

Ullmann's Encyclopedia of Industrial Chemistry, 1993, vol. A24, pp. 34–35.
J. Org. Chem. 1982, 47, 3966–3969.

* cited by examiner

*Primary Examiner*—Margaret G. Moore
(74) *Attorney, Agent, or Firm*—Brooks & Kushman P.C.

(57) ABSTRACT

The invention relates to organosilicon compounds with at least three silicon atoms, consisting of units of the formula (I) $R_aSi(NR^1C=ONR^2_2)_k(NR^3C=ONR^4)_{t/2}Y_mO_{n/2}[(CR^5_2)_s]_{r/2}$, where Y represents units of the formula (II) $-SiR^6_{3-p-q}(NR^1C=ONR^2_2)_p(NR^3C=ONR^4)_{q/2}$, where R, $R^1$, $R^2$, $R^3$, $R^4$, $R^5$ and $R^6$ independently of each other can be either identical or different and represent a hydrogen atom or possibly substituted monovalent hydrocarbon radicals with between 1 and 20 carbon atoms; and where a, k, t, n, m, r, s, p and q have the meaning assigned to them in claim 1, under the provision that the sum of p+q is ≦3, the sum of a+k+l+m+n+r equals 4, the sum of m+r equals 0 or 1, and the organosilicon compound of the invention contains at least one unit of formula (I) where t is not equal to 0.

11 Claims, No Drawings

ORGANOSILICON COMPOUNDS HAVING UREA GROUPS, METHOD FOR PRODUCING SAME AND THEIR UTILIZATION

TECHNICAL FIELD

The invention relates to organosilicon compounds which contain urea groups linked via Si—N bonds, their preparation and their use.

DESCRIPTION OF THE RELATED ART

Silylation products of urea, such as, for example, N,N'-bis(trimethylsilyl)urea and derivatives thereof, are already known. In this context, reference may be made, for example, to U.S. Pat. No. 3,346,609 (General Electric Co.; published on Oct. 10, 1967). U.S. Pat. No. 3,239,489 (Monsanto Co.; published on Mar. 8, 1966) describes polymers which consist of the sequence -silane unit-urea unit-hydrocarbon chain- which can be prepared by reaction of silazanes with diisocyanates. U.S. Pat. No. 4,959,407 (General Electric Co.; published on Sep. 25, 1990) furthermore discloses siloxane chains which are blocked on the ends by urea units and have a maximum of 10 siloxane units as chain lengtheners.

SUMMARY OF THE INVENTION

The invention pertains to organosilicon compounds having at least three silicon atoms and which contain urea groups bonded via Si—N bonds. The urea group-containing organosilicon compounds are useful in preparing moisture curable RTV-1 compositions, and are useful in diverse processes where scavenging of protic materials, particularly water, is desired. The invention also pertains to processes for the preparation of the Si—N linked, urea group-containing organosilicon compounds.

DESCRIPTION OF THE PREFERRED EMBODIMENTS

The invention relates to organosilicon compounds having at least three silicon atoms, of units of the formula $$R_a Si(NR^1C\!=\!ONR^2{}_2)_k(NR^3C\!=\!ONR^4)_{t/2}Y_m O_{n/2}[(CR^5{}_2)_s]_{r/2} \quad (I)$$

where Y is units of the formula $$-\!SiR^6{}_{3-p-q}(NR^1C\!=\!ONR^2{}_2)_p(NR^3C\!=\!ONR^4)_{q/2} \quad (II),$$

in which R, $R^1$, $R^2$, $R^3$, $R^4$, $R^5$ and $R^6$ independently of one another can in each case be identical or different and are a hydrogen atom or optionally substituted monovalent hydrocarbon radicals having 1 to 20 carbon atoms, a is 0, 1, 2 or 3,
k is 0, 1, 2 or 3,
t is 0, 1, 2, 3 or 4,
n is 0, 1, 2, 3 or 4,
m is 0 or 1,
r is 0 or 1,
s is an integer from 1 to 20,
p is 0, 1, 2 or 3 and
q is 0, 1, 2 or 3, with the proviso that
the sum p+q is $\leq 3$,
the sum a+k+t+m+n+r is 4,
the sum m +r is 0 or 1 and
the organosilicon compound according to the invention contains at least one unit of the formula (I) where t is other than 0.

Although expressed by the formulae (I) and (II), it is to be stated again that all the radicals characterized by the indices a, k, t, m, n, r, p and q are Si-bonded radicals, and the radicals —(NR$^3$C=ONR$^4$)—, —O— and —(CR$^5{}_2$)$_s$— in each case have 2 Si bonds.

Preferably, in the units of the formula (I), the sum k+t+n is other than 0.

Examples of hydrocarbon radicals R and $R^6$ are alkyl radicals, such as the methyl, ethyl, n-propyl, isopropyl, 1-n-butyl, 2-n-butyl, isobutyl, tert-butyl, n-pentyl, isopentyl, neopentyl or tert-pentyl radical; hexyl radicals, such as the n-hexyl radical; heptyl radicals, such as the n-heptyl radical; octyl radicals, such as the n-octyl radical and iso-octyl radicals, such as the 2,2,4-trimethylpentyl radical; nonyl radicals, such as the n-nonyl radical; decyl radicals, such as the n-decyl radical; dodecyl radicals, such as the n-dodecyl radical; and octadecyl radicals, such as the n-octadecyl radical; alkenyl radicals, such as the vinyl and the allyl radicals; cycloalkyl radicals, such as cyclopentyl, cyclohexyl and cycloheptyl radicals and methylcyclohexyl radicals; aryl radicals, such as the phenyl, naphthyl, anthryl and phenanthryl radical; alkaryl radicals, such as o-, m- and p-tolyl radicals, xylyl radicals and ethylphenyl radicals; and aralkyl radicals, such as the benzyl radical and the α- and the β-phenylethyl radical.

Examples of substituted hydrocarbon radicals R and $R^6$ are halogenated radicals, such as the 3-chloro-propyl radical, the 3,3,3-trifluoropropyl radical, chlorophenyl radicals and hexafluoropropyl radicals, such as the 1-trifluoromethyl-2,2,2-trifluoroethyl radical; the 2-(perfluorohexyl)ethyl radical, the 1,1,2,2-tetra-fluoroethyloxypropyl radical, the 1-trifluoromethyl-2,2,2-trifluoroethyloxypropyl radical, the perfluoroiso-propyloxyethyl radical and the perfluoroisopropyloxy-propyl radical; radicals substituted by amino groups, such as the N-(2-aminoethyl)-3-aminopropyl radical, the 3-aminopropyl radical and the 3-(cyclohexylamino)propyl radical, 3-(N,N-diethyl-2-aminoethylamino)propyl radical and 3-(butylamino)propyl radical and 3-(3-methoxypropylamino)propyl radical; ether-functional radicals, such as the 3-methoxypropyl radical and the 3-ethoxypropyl radical; cyano-functional radicals, such as the 2-cyano-ethyl radical; ester-functional radicals, such as the methacryloxypropyl radical; epoxy-functional radicals, such as the glycidoxypropyl radical; sulfur-functional radicals, such as the 3-mercaptopropyl radical; and radicals substituted by (poly)glycol groups, it being possible for the latter to be built up from oxyethylene and/or oxypropylene units.

Preferred radicals R and $R^6$ are, in each case independently of one another, hydrocarbon radicals having 1 to 10 carbon atoms, hydrocarbon radicals having 1 to 10 carbon atoms which are substituted by amino groups or by fluorine radicals, and optionally substituted amino and glycidoxy groups which are bonded to the silicon atom via alkylene radicals having 2 to 6 carbon atoms.

The radicals R and $R^6$ are particularly preferably, in each case independently of one another, alkyl radicals and alkenyl radicals having 1 to 4 carbon atoms, such as the methyl and the vinyl radical, and optionally substituted amino and glycidoxy groups which are bonded to the silicon atom via alkylene radicals having 2 to 6 carbon atoms, such as, for example, the 3-(2-aminoethylamino)propyl radical, the 3-(cyclohexylamino)propyl radical or the 3-(glycidoxy) propyl radical.

Both R and $R^6$ are, in particular, the methyl radical.

Examples of radicals $R^1$, $R^2$, $R^3$ and $R^4$ as optionally substituted hydrocarbon radicals are the examples given above for radical R and $R^6$.

Preferred radicals $R^1$, $R^2$, $R^3$ and $R^4$ are, in each case independently of one another, hydrogen and hydrocarbon radicals having 1 to 10 carbon atoms.

The radicals $R^1$, $R^2$, $R^3$ and $R^4$ are particularly preferably, independently of one another, a hydrogen atom or the methyl radical.

Examples of the radical $R^5$ are the examples given above for radical R and $R^6$.

The radical $R^5$ is preferably a hydrogen atom or hydrocarbon radicals having 1 to 10 carbon atoms, as well as amino-functional and fluorine-substituted hydrocarbon radicals; $R^5$ particularly preferably being a hydrogen atom.

a is preferably 1, 2 or 3.
k is preferably 0, 1 or 2.
t is preferably 1, 2 or 3.
n is preferably 1 or 2.
s is preferably 2.
p is preferably 0, 1 or 2.
q is preferably 1 or 2.

Examples of the units of the formula (I) are

1a) $Me_3Si(NH-C=O-NH)_{1/2}$; $Me_2Si(NH-C=O-NH)_{2/2}$; $MeSi(NH-C=O-NH)_{3/2}$; $Si(NH-C=O-NH)_{4/2}$;

1b) $Me_3Si(NMe-C=O-NMe)_{1/2}$; $Me_2Si(NMe-C=O-NMe)_{2/2}$; $MeSi(NMe-C=O-NMe)_{3/2}$; $Si(NMe-C=O-NMe)_{4/2}$;

2) $Me_3SiO_{1/2}$; $Me_2SiO_{2/2}$; $MeSiO_{3/2}$; $SiO_{4/2}$;

3) $Me_3Si[SiMe(NH-C=O-NH)_{1/2}(NH-C=O-NH_2)]$; $Me_3Si[SiMe(NH-C=O-NH)_{2/2}]$; $Me_3Si[SiMe_2(NH-C=O-NH)_{1/2}]$;

4) $Me_3Si[(CMe_2)s]_{1/2}$;

5) $Me_2Si(NH-C=O-NH)_{1/2}(NH-C=O-NH_2)$ $MeSi(NH-C=O-NH)_{2/2}(NH-C=O-NH_2)$; $MeSi(NH-C=O-NH)_{1/2}(NH-C=O-NH_2)_2$; $Si(NH-C=O-NH)_{3/2}(NH-C=O-NH_2)$; $Si(NH-C=O-NH)_{2/2}(NH-C=O-NH_2)_2$; $Si(NH-C=O-NH)_{1/2}(NH-C=O-NH_2)_3$;

6) $Me_2Si(NH-C=O-NH)_{1/2}O_{1/2}$; $MeSi(NH-C=O-NH)_{2/2}O_{1/2}$; $MeSi(NH-C=O-NH)_{1/2}O_{2/2}$; $Si(NH-C=O-NH)_{3/2}O_{1/2}$; $Si(NH-C=O-NH)_{2/2}O_{2/2}$; $Si(NH-C=O-NH)_{1/2}O_{3/2}$;

7) $Me_2Si[SiMe(NH-C=O-NH)_{1/2}(NH-C=O-NH_2)](NH-C=O-NH)_{1/2}$; $Me_2Si[SiMe(NH-C=O-NH)_{2/2}](NH-C=O-NH)_{1/2}$; $Me_2Si[SiMe_2(NH-C=O-NH)_{1/2}](NH-C=O-NH)_{1/2}$; $Me_2Si[SiMe_2(NH-C=O-NH_2)](NH-C=O-NH)_{1/2}$; $MeSi[SiMe(NH-C=O-NH)_{1/2}(NH-C=O-NH_2)](NH-C=O-NH)_{2/2}$; $MeSi[SiMe(NH-C=O-NH)_{2/2}](NH-C=O-NH)_{2/2}$; $Si[SiMe(NH-C=O-NH)_{1/2}(NH-C=O-NH_2)](NH-C=O-NH)_{3/2}$; $Si[SiMe(NH-C=O-NH)_{2/2}](NH-C=O-NH)_{3/2}$;

8) $Me_2Si[(CMe_2)_s]_{1/2}(NH-C=O-NH)_{1/2}$; $MeSi[(CMe_2)_s]_{1/2}(NH-C=O-NH)_{2/2}$; $Si[(CMe_2)_s]_{1/2}(NH-C=O-NH)_{3/2}$; where s=1 to 20

9). $Me_2SiO_{1/2}(NH-C=O-NH_2)$; $MeSiO_{2/2}(NH-C=O-NH_2)$; $MeSiO_{1/2}(NH-C=O-NH_2)_2$; $SiO_{3/2}(NH-C=O-NH_2)$; $SiO_{2/2}(NH-C=O-NH_2)_2$; $SiO_{1/2}(NH-C=O-NH_2)_3$;

10) $Me_2Si[SiMe(NH-C=O-NH_2)](NH-C=O-NH_2)$; $Me_2Si[SiMe(NH-C=O-NH)_{2/2}](NH-C=O-NH_2)$; $Me_2Si[SiMe_2(NH-C=O-NH)_{1/2}](NH-C=O-NH_2)$; $Me_2Si[SiMe_2(NH-C=O-NH_2)](NH-C=O-NH_2)$; $MeSi[SiMe(NH-C=O-NH)_{1/2}(NH-C=O-NH_2)](NH-C=O-NH_2)_2$; $MeSi[SiMe(NH-C=O-NH)_{2/2}](NH-C=O-NH_2)_2$; $Si[SiMe(NH-C=O-NH)_{1/2}(NH-C=O-NH_2)](NH-C=O-NH_2)_3$; $Si[SiMe(NH-C=O-NH)_{2/2}](NH-C=O-NH_2)_3$;

11) $Me_2Si[(CMe_2)_s]_{1/2}(NH-C=O-NH_2)$; $MeSi[(CMe_2)_s]_{1/2}(NH-C=O-NH_2)_2$; $Si[(CMe_2)_s]_{1/2}(NH-C=O-NH_2)_3$; where s=1 to 20

12) $Me_2Si[SiMe(NH-C=O-NH)_{1/2}(NH-C=O-NH_2)]O_{1/2}$; $Me_2Si[SiMe(NH-C=O-NH)_{2/2}]O_{1/2}$; $Me_2Si[SiMe_2(NH-C=O-NH)_{1/2}]O_{1/2}$; $Me_2Si[SiMe_2(NH-C=O-NH_2)]O_{1/2}$; $Me_2Si[SiMe(NH-C=O-NH)_{1/2}O_{1/2}]O_{1/2}$; $Me_2Si[SiMeO_{2/2}]O_{1/2}$; $Me_2Si[SiMe(NH-C=O-NH_2)O_{1/2}]O_{1/2}$; $Me_2Si[SiMe_2O_{1/2}]O_{1/2}$; $MeSi[SiMe(NH-C=O-NH)_{1/2}(NH-C=O-NH_2)]O_{2/2}$; $MeSi[SiMe(NH-C=O-NH)_{2/2}]O_{2/2}$; $MeSi[SiMe(NH-C=O-NH)_{1/2}O_{1/2}]O_{2/2}$; $MeSi[SiMe(NH-C=O-NH_2)O_{1/2}]O_{2/2}$; $MeSi[SiMeO_{2/2}]O_{2/2}$; $Si[SiMe(NH-C=O-NH)_{1/2}(NH-C=O-NH_2)]O_{3/2}$; $Si[SiMe(NH-C=O-NH)_{2/2}]O_{3/2}$; $Si[SiMe(NH-C=O-NH)_{1/2}O_{1/2}]O_{3/2}$; $Si[SiMe(NH-C=O-NH_2)O_{1/2}]O_{3/2}$; $Si[SiMeO_{2/2}]O_{3/2}$;

13) $Me_2Si[(CMe_2)_s]_{1/2}O_{1/2}$; $MeSi[(CMe_2)_s]_{1/2}O_{2/2}$; $Si[(CMe_2)_s]_{1/2}O_{3/2}$; where s=1 to 20

14) $MeSiO_{1/2}(NH-C=O-NH)_{1/2}(NH-C=O-NH_2)$; $SiO_{2/2}(NH-C=O-NH)_{1/2}(NH-C=O-NH_2)$; $SiO_{1/2}(NH-C=O-NH)_{2/2}(NH-C=O-NH_2)$; $SiO_{1/2}(NH-C=O-NH)_{1/2}(NH-C=O-NH_2)_2$;

15) $MeSi[SiMe(NH-C=O-NH)_{1/2}(NH-C=O-NH_2)](NH-C=O-NH)_{1/2}(NH-C=O-NH_2)$; $MeSi[SiMe(NH-C=O-NH)_{2/2}](NH-C=O-NH)_{1/2}(NH-C=O-NH_2)$; $Si[SiMe(NH-C=O-NH)_{1/2}(NH-C=O-NH_2)](NH-C=O-NH)_{1/2}(NH-C=O-NH_2)_2$; $Si[SiMe(NH-C=O-NH)_{2/2}](NH-C=O-NH)_{1/2}(NH-C=O-NH_2)_2$; $Si[SiMe(NH-C=O-NH)_{1/2}(NH-C=O-NH_2)](NH-C=O-NH)_{2/2}(NH-C=O-NH_2)$; $Si[SiMe(NH-C=O-NH)_{2/2}](NH-C=O-NH)_{2/2}(NH-C=O-NH_2)$

16) $MeSi[(CMe_2)_s]_{1/2}(NH-C=O-NH)_{1/2}(NH-C=O-NH_2)$; $Si[(CMe_2)_s]_{1/2}(NH-C=O-NH)_{2/2}(NH-C=O-NH_2)$ $Si[(CMe_2)_s]_{1/2}(NH-C=O-NH)_{1/2}(NH-C=O-NH_2)_2$; where s=1 to 20

17) $MeSi[SiMe(NH-C=O-NH)_{1/2}(NH-C=O-NH_2)](NH-C=O-NH)_{1/2}O_{1/2}$; $MeSi[SiMe(NH-C=O-NH)_{2/2}](NH-C=O-NH)_{1/2}O_{1/2}$; $Si[SiMe(NH-C=O-NH)_{1/2}(NH-C=O-NH_2)](NH-C=O-NH)_{1/2}O_{2/2}$; $Si[SiMe(NH-C=O-NH)_{1/2}(NH-C=O-NH_2)](NH-C=O-NH)_{2/2}O_{1/2}$; $Si[SiMe(NH-C=O-NH)_{2/2}](NH-C=O-NH)_{1/2}O_{2/2}$; $Si[SiMe(NH-C=O-NH)_{2/2}](NH-C=O-NH)_{2/2}O_{1/2}$; $Si[SiMe(NH-C=O-NH)_{2/2}](NH-C=O-NH)_{2/2}O_{1/2}$

18) $MeSi[(CMe_2)_s]_{1/2}(NH-C=O-NH)_{1/2}O_{1/2}$; $Si[(CMe_2)_s]_{1/2}(NH-C=O-NH)_{2/2}O_{1/2}$; $Si[(CMe_2)_s]_{1/2}(NH-C=O-NH)_{1/2}O_{2/2}$; where s=1 to 20

19) $MeSi[SiMe(NH-C=O-NH)_{1/2}(NH-C=O-NH_2)]]O_{1/2}(NH-C=O-NH_2)$; $MeSi[SiMe(NH-C=O-NH)_{2/2}]O_{1/2}(NH-C=O-NH_2)$; $Si[SiMe(NH-C=O-NH)_{1/2}(NH-C=O-NH_2)]O_{1/2}(NH-C=O-NH_2)_2$; $Si[SiMe(NH-C=O-NH)_{2/2}]O_{1/2}(NH-C=O-NH_2)_2$; $Si[SiMe(NH-C=O-NH)_{1/2}(NH-C=O-NH_2)]O_{2/2}(NH-C=O-NH_2)$; $Si[SiMe(NH-C=O-NH)_{2/2}]O_{2/2}(NH-C=O-NH_2)$

20) $MeSi[(CMe_2)_s]_{1/2}O_{1/2}(NH-C=O-NH_2)$; $Si[(CMe_2)_s]_{1/2}O_{2/2}(NH-C=O-NH_2)$; $Si[(CMe_2)_s]_{1/2}O_{1/2}(NH-C=O-NH_2)_2$; where s =1 to 20

21) $Si[SiMe(NH-C=O-NH)_{1/2}(NH-C=O-NH_2)]O_{1/2}(NH-C=O-NH_2)(NH-C=O-NH)_{1/2}$; $Si[SiMe(NH-C=O-NH)_{2/2}]O_{1/2}(NH-C=O-NH_2)(NH-C=O-NH)_{1/2}$;

22) $Si[(CMe_2)_s]_{1/2}O_{1/2}(NH-C=O-NH_2)(NH-C=O-NH)_{1/2}$; where s=1 to 20, in which Me is the methyl radical.

Examples of the compounds according to the invention of units of the formula (I) are a) [Me$_3$Si(NH—C=O—NH)][SiMe$_2$O]$_x$[SiMe$_2$—NH—C=O—NH—]$_y$[SiMe$_3$] where x=0–1000; y=0–500; x+y≧1; [Me$_3$Si(OSiMe$_2$)$_4$(NH—C=O—NH)][SiMe$_2$ O]$_x$[SiMe$_2$—NH—C=O—NH—]$_y$[(SiMe$_2$O)$_4$SiMe$_3$] where x=0–1000; y=0–500; x+y≧1; (Me$_3$Si(NMe—C=O—NMe)][SiMe$_2$O]$_x$[SiMe$_2$(NMe—C=O—NMe)]$_y$[SiMe$_3$] where x=0–1000; y=0–500; x+y>1; [Me$_3$Si(OSiMe$_2$)$_4$(NMe—C=O—NMe)][SiMe$_2$O]$_x$[SiMe$_2$(NMe—C=O—NMe)]$_y$ [(SiMe$_2$O)$_4$SiMe$_3$] where x=0–1000; y=0–500; x+y≧1; [MeSi(NH—C=O—NH)$_{2/2}$(NH—C=O—NH$_2$)][MeSi(NH—C=O—NH)$_{3/2}$]$_2$; [MeSi (NH—C=O—NH)$_{1/2}$(NH—C=O—NH$_2$)$_{2/2}$[MeSi(NH—C=O—NH)$_{2/2}$(NH—C=O—NH$_2$)]$_3$[MeSi(NH—C=O—NH)$_{3/2}$]$_{12}$; [MeSi (NPh—C=O—NPh)$_{1/2}$(NPh—C—O=NPh$_2$)$_2$]$_2$[MeSi (NPh—C=O—NPh)$_{2/2}$ (NPh—C=O—NPh$_2$)]$_3$(MeSi (NPh—C=O—NPh)$_{3/2}$]$_{12}$; [ViSi(NH—C=O—NH)$_{1/2}$(NH—C=O—NH$_2$)$_2$]$_2$[ViSi(NH—C=O—NH)$_{2/2}$(NH—C=O—NH$_2$)]$_3$[ViSi(NH—C=O—NH)$_{3/2}$]$_{12}$; [MeSi(NH—C=O—NH)$_{1/2}$(NH—C=O—NH$_2$)$_2$]$_2$[MeSi(NH—C=O—NH)$_{2/2}$(NH—C=O—NH$_2$)]$_2$[MeSi (NH—C=O—NH)$_{3/2}$]$_2$[(NH—C=O—NH)$_{1/2}$(SiMe$_2$O)$_x$SiMe$_2$(NH—C=O—NH)$_{1/2}$]$_y$ where x=0–20; y=0–50; [ViSi (NH—C=O—NH)$_{1/2}$(NH—C=O—NH$_2$)$_2$]$_2$[ViSi(NH—C=O—NH)$_{2/2}$(NH—C=O—NH$_2$)]$_2$[ViSi(NH—C=O—NH)$_{3/2}$]$_2$[(NH—C=O—NH)$_{1/2}$(SiMe$_2$O)$_x$SiMe$_2$(NH—C=O—NH)$_{1/2}$]$_y$ where x=0 to 20; y=0 to 50;

b) [MeSi(NH—C=O—NH)$_{2/2}${SiMe(NH—C=O—NH)$_{1/2}$(NH—C=O—NH$_2$)}]$_7$ [MeSi (NH—C=O—NH)$_{1/2}$(NH—C=O—NH$_2$){SiMe(NH—C=O—NH)$_{1/2}$(NH—C=O—NH$_2$)}]$_4$ [MeSi(NH—C=O—NH)$_{2/2}${SiMe (NH—C=O—NH$_2$)$_2$}]$_3$ [MeSi(NH—C=O—NH)$_{2/2}${SiMe(NH—C=O—NH)$_{2/2}$}$_2$[MeSi(NH—C=O—NH)$_{1/2}$(NH—C=O—NH$_2$){SiMe(NH—C=O—NH$_2$)$_2$}]; [MeSi(NH—C=O—NH)$_{2/2}${SiMe(NH—C=O—NH)$_{1/2}$(NH—C—O—NH$_2$)}]$_3$ [MeSi(NH—C=O—NH)$_{1/2}$(NH—C=O—NH$_2$){SiMe(NH—C=O—NH)$_{1/2}$ (NH—C=O—NH$_2$)}]$_6$ [MeSi(NH—C=O—NH)$_{2/2}${SiMe(NH—C=O—NH$_2$)2}$_4$ [MeSi(NH—C=O—NH)$_{2/2}$(SiMe(NH—C=O—NH$_{2/2}$}]$_2$ [MeSi (NH—C=O—NH)$_{1/2}$(NH—C=O—NH$_2$){SiMe(NH—C=O—NH$_2$)$_2$}][SiMe$_2$(NH—C=O—NH)$_{2/2}$]$_{20}$;

c) [MeSi{(CH$_2$)$_2$}$_{1/2}$(NH—C=O—NH)$_{1/2}$(NH—C=O—NH$_2$)]$_5$ [MeSi{(CH$_2$)$_2$}$_{1/2}$(NH—C=O—NH)$_{2/2}$]$_4$ [MeSi{(CH$_2$)$_2$}$_{1/2}$(NH—C=O—NH)$_2$][SiMe$_2$(NH—C=O—NH)$_{2/2}$]$_{10}$, where Me is the methyl radical, Vi is the vinyl radical and Ph is the phenyl radical.

The organosilicon compounds according to the invention preferably contain 3 to 1000 silicon atoms, particularly preferably 3 to 300 silicon atoms.

The organosilicon compounds according to the invention of units of the formula (I) are preferably those in which r is 0.

The organosilicon compounds according to the invention of units of the formula (I) are particularly preferably those in which r=m=0.

The compounds according to the invention can be prepared by various routes.

Process A

The invention also relates to a process for the preparation of the organosilicon compounds according to the invention by reaction of urea (derivatives) of the formula

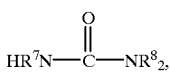

(III)

in which $R^7$ and $R^8$ can be identical or different and in each case independently of one another have a meaning given above for $R^1$, $R^2$, $R^3$ and $R^4$, with the proviso that at least one compound of the formula (III) having at least one radical $R^8$ which is a hydrogen atom is employed, with organosilicon compounds containing chlorine radicals, of units of the formula

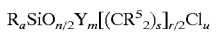

(IV), in which R, $R^5$ Y, a, n, m, r and s can in each case be identical or different and have a meaning given above for these symbols; and u is 0, 2, 3 or 4, with the proviso that the sum a+n+m+r+u is 4 and at least one compound of units of the formula (IV) having at least one chlorine atom per molecule is present, HCl being split off.

The HCl formed in this reaction is preferably removed.

Examples of the urea (derivatives) employed in process A according to the invention are urea, N-methyl-urea, N,N'-dimethylurea, N-vinylurea, N,N'-divinylurea, N-phenylurea, N,N'-diphenylurea, N-ethylurea, N,N'-diethylurea, N-(trifluoropropyl)urea, N,N'-di(trifluoropropyl)urea, N-cyclohexylurea, N,N'-dicyclohexylurea, N-benzylurea and N,N'-dibenzylurea, urea being particularly preferred.

The compounds containing chlorine radicals employed in process A according to the invention can be monomeric, oligomeric or polymeric compounds, where the nature and amount is, of course, to be chosen such that the organosilicon compounds formed contain at least 3 silicon atoms.

Examples of the organosilicon compounds which contain chlorine radicals and are employed in process A according to the invention are a) Me$_3$Si(OSiMe$_2$)$_e$Cl; Cl(SiMe$_2$O)$_e$SiMe$_2$Cl; MeSiCl$_3$; SiCl$_4$ where e is 0 to 1000;

b) ViMe$_2$Si(OSiMe$_2$)$_e$OSiViMe)$_f$Cl; Cl(SiMe$_2$O)$_e$(SiViMeO)$_f$SiMe$_2$Cl; ViSiCl$_3$ where e is 0 to 1000 and f is 0 to 100;

c) PhMe$_2$Si(OSiMe$_2$)$_e$(OSiPhMe)$_f$Cl; Cl(SiMe$_2$O)$_e$(SiPhMeO)$_f$SiMe$_2$Cl; PhSiCl$_3$ where e is 0 to 1000 and f is 0 to 100; (trifluoropropyl)Me$_2$Si (OSiMe$_2$)$_e$(OSi(trifluoropropyl)Me)$_f$Cl; Cl(SiMe$_2$O)$_e$(Si(trifluoropropyl)MeO)$_f$SiMe$_2$Cl; (trifluoropropyl)SiCl$_3$ where e is 0 to 1000 and f is 0 to 100; and d) Cl$_3$Si—(CH$_2$)$_s$—SiCl$_3$; MeCl$_2$Si—(CH$_2$)$_s$—SiMeCl$_2$; ClMe$_2$Si—(CH$_2$)$_s$—SiClMe$_2$ where s is 1 to 20; disilanes of the formula Me$_{6-g}$Si$_2$Cl$_g$ where g is 1 to 6, the examples mentioned under a), b) and c) being preferred and Me$_3$Si(OSiMe$_2$)$_e$Cl, Cl(SiMe$_2$O)$_e$SiMe$_2$Cl, MeSiCl$_3$ and SiCl$_4$, where e is 0 to 1000, being particularly preferred, and where Me is the methyl radical, Vi is the vinyl radical and Ph is the phenyl radical.

The urea (derivative) is preferably employed in process A according to the invention in amounts of 0.01 to 10 mol, particularly preferably 0.1 to 2 mol, in each case per mole of chlorine of the organosilicon compounds containing chlorine radicals employed according to the invention.

Both the organosilicon compounds containing chlorine radicals employed according to the invention and the urea (derivatives) are commercially available products or can be prepared by methods customary in chemistry. In this context, reference may be made, for example, to the preparation processes described in U.S. Pat. No. 5,473,037 and in EP-A 484 959.

Process A according to the invention is carried out at temperatures of preferably −80 to 200° C., particularly preferably 0 to 80° C., and preferably under the pressure of the surrounding atmosphere, that is to say between 900 and 1100 hPa.

Process A according to the invention is preferably carried out in an inert atmosphere, an atmosphere which is essentially free from oxygen and water, such as, for example, a nitrogen or argon atmosphere, being described as an inert atmosphere in the context of the invention.

The reaction according to the invention is preferably carried out in the presence of solvents which are inert towards the reaction participants, such as, for example, aromatics, hydrocarbons, ethers, chlorinated hydrocarbons or α,ω-trimethylsilylpolydimethylsiloxanes, the solvents optionally employed preferably being largely free from water or containing water in amounts of up to 0.2% by weight.

If a solvent is employed in process A according to the invention, preferred solvents are ethers and optionally substituted hydrocarbons, such as, for example, benzene, toluene, xylene, chloroform, methylene chloride, trichloroethane, trichloropropane, hexane, heptane, octane, decane, dodecane, petroleum ether, diethyl ether and tetrahydrofuran.

If a solvent is employed, the amounts are preferably 1 to 1000 parts by weight, particularly preferably 20 to 400 parts by weight, in each case per 100 parts by weight of organosilicon compound containing chlorine radicals.

The hydrogen chloride formed in the reaction according to the invention is preferably removed by means of bases, such as, for example, ammonia, methylamine, dimethylamine, trimethylamine, ethylamine, diethylamine, triethylamine, butylamine, dibutylamine, tributylamine, octylamine, dioctylamine, trioctylamine, nonylamine, dinonylamine and trinonylamine.

Bases which are employed in process A according to the invention are preferably amines, particularly preferably tertiary amines, such as, for example, triethylamine or pyridine.

If a base is employed in process A according to the invention, the amounts are preferably 0.1 to 20 mol, particularly preferably 0.5 to 5 mol, in each case per mole of chlorine of the organosilicon compound containing chlorine radicals employed according to the invention.

The salt formed by the trapping reaction, preferably an ammonium hydrogen chloride, such as, for example, triethylammonium chloride, is preferably removed from the reaction mixture, for example, by filtration or centrifugation. If desired, the filtrate is freed from the organic solvent optionally employed, for example by distillation.

In a preferred embodiment of process A according to the invention, the organosilicon compounds containing chlorine radicals are added to a mixture of urea (derivatives), if appropriate base and, if appropriate, organic solvent, and the components are allowed to react.

In a particularly preferred embodiment of process A according to the invention, the organosilicon compounds containing chlorine radicals are added to a mixture of urea (derivatives), base and organic solvent, and the components are allowed to react, the salt formed being filtered off and the organic solvent separated off when the reaction has ended.

The components employed in process A according to the invention can in each case be an individual type of such a component or at least two different types of such components. The organosilicon compound containing chlorine radicals employed according to the invention is preferably a mixture of different types.

Process B

The invention also relates to a process for the preparation of the organosilicon compounds according to the invention, which comprises in a 1st step reacting organosilicon compounds containing chlorine radicals, of units of the formula (IV), with the proviso that the sum a+n+m+r+u is 4, and at least one compound of units of the formula (IV) having at least one chlorine atom per molecule is present, with amino compounds of the formula $$R^9{}_2NH \quad (V)$$

in which $R^9$ can be identical or different and has a meaning given for the radical R, and in a 2nd step reacting the organosilicon compounds obtained in the 1st step with urea (derivatives) of the formula (III), with the proviso that at least one compound of the formula (III) having at least one radical $R^8$ which is a hydrogen atom is employed, if appropriate in the presence of catalysts.

The radical $R^9$ is preferably a hydrogen atom or alkyl radicals having 1 to 20 carbon atoms, a hydrogen atom and alkyl radicals having 1 to 4 carbon atoms being particularly preferred.

Examples of amino compounds of the formula (V) are ammonia, methylamine, dimethylamine, ethylamine, diethylamine, propylamine, dipropylamine, butylamine, dibutylamine, pentylamine, dipentylamine, octylamine, nonylamine, decylamine, coconut fatty amine, oleylamine, stearylamine, tallow fatty amine, cyclohexylamine, benzylamine, phenylethylamine, ethylenediamine, diaminobutane, diaminohexane, aniline, methylaniline, diphenylaniline, toluidine, chloranil, nitroaniline and phenylenediamine, ammonia, methylamine, dimethylamine, ethylamine, diethylamine, propylamine, dipropylamine, butylamine and dibutylamine being preferred and ammonia and methylamine being particularly preferred.

The organosilicon compounds containing chlorine radicals, of units of the formula (IV), can be the same as described for process A, where the nature and amount are, of course, to be chosen such that the organosilicon compounds formed contain at least 3 silicon atoms.

In the 1st step of process B according to the invention, the amino compound of the formula (V) is employed in amounts of preferably 0.5 to 10 mol, particularly preferably 0.8 to 5 mol, in each case per mole of chlorine of the organosilicon compound containing chlorine radicals employed according to the invention.

The reaction according to the 1st step of process B according to the invention can furthermore be carried out in a manner already known. Thus, the reaction of chlorosiloxanes with ammonia or amines is described, for example, in DE-A 29 53 680 and in the literature cited therein.

The urea (derivatives) of the formula (III) can be the same as described for process A.

In the 2nd step of process B according to the invention, all those catalysts which have been used hitherto as a catalyst for the reaction of hexamethyldisilazane with urea to give N,N'-bis(trimethylsilyl)urea can be employed. Examples of these catalysts are to be found in DE-A 25 07 882, DE-A 25 53 932, DE-A 27 57 936, Bruynes et al. in J. org. Chem. 1982, 47, 3966–9 and Ullmann's Encyclopedia of Industrial Chemistry, 1993, Volume A 24, page 34f.

If a catalyst is employed in the 2nd step of process B according to the invention, it is preferably one such as is used in DE-A 25 07 882, $(NH_4)_2SO_4$ being particularly preferred.

If a catalyst is employed in the 2nd step of process B according to the invention, the amounts are preferably 0.001 to 1 part by weight per 100 parts by weight of organosilicon compound containing chlorine radicals employed according to the invention.

The 1st step of process B according to the invention is carried out at temperatures of preferably −20 to 200° C., particularly preferably 0 to 150° C., in particular 0 to 100° C.

The 2nd step of process B according to the invention is carried out at temperatures of preferably 0 to 200° C., particularly preferably 20 to 180° C., in particular 40 to 160° C.

The 1st step of process B according to the invention is preferably carried out under the pressure of the surrounding atmosphere, that is to say between 900 and 1100 hPa.

The 2nd step of process B according to the invention is preferably carried out under pressures of between 1 hPa and normal pressure, that is to say between 900 and 1100 hPa.

The 2nd step of the reaction according to the invention can be carried out in the presence of solvents which are inert toward the reaction participants, but this is not preferred. Examples of these are all the solvents mentioned in connection with process A.

In a preferred embodiment of process B according to the invention, in a 1st step amine is added to a mixture of organosilicon compounds containing chlorine radicals and organic solvent and the components are allowed to react, the salt formed being separated off when the reaction has ended, and in a 2nd step urea (derivatives), if appropriate mixed with catalyst, are added to the organosilicon compound obtained in the 1st step and the components are allowed to react.

The components employed in process B according to the invention can in each case be an individual type of such a component or at least two different types of such components. The organosilicon compound containing chlorine radicals employed according to the invention is preferably a mixture of different types.

Process C

The invention relates to a process for the preparation of the organosilicon compounds according to the invention by reaction of silylated urea (derivatives) of the formula

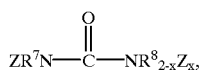

(VI)

in which $R^7$ and $R^8$ have one of the meanings given above for these radicals, Z is a silyl radical and x is 0 or 1, with the proviso that the compound of the formula (VI) contains not more than 2 silicon atoms and at least one compound of the formula (VI) where x=1 is employed, with organosilicon compounds containing chlorine radicals, of units of the formula (IV), with the proviso that the sum a+n+m+r+u is 4 and at least one compound of units of the formula (IV) having at least one chlorine atom per molecule is present.

Examples of radicals Z are $Me_3Si—$, $Et_3Si—$, $ViMe_2Si—$, $PhMe_2Si—$, $(H_4F_3C_3)Me_2Si—$, $(H_4F_3C_3)_3Si—$ and $Me_3SiOMe_2Si—$, where Me is the methyl radical, Vi is the vinyl radical, Et is the ethyl radical and Ph is the phenyl radical.

Examples of silylated urea (derivatives) employed in process C according to the invention are N,N'-bis(trimethylsilyl)urea, N,N'-bis(trimethylsilyl)-N,N'-dimethylurea and N,N'-bis(trimethylsilyl)-N,N'-diphenylurea, N,N'-bis(trimethylsilyl)urea being particularly preferred.

The silylated urea (derivatives) employed in process C according to the invention are commercially available compounds or can be prepared by processes customary in silicon chemistry.

Examples of the organosilicon compounds containing chlorine radicals, of units of the formula (IV) employed in process C according to the invention are those mentioned in connection with process A, where the nature and amount are, of course, to be chosen such that the corresponding organosilicon compounds contain at least three silicon atoms.

The silylated compound of the formula (VI) is employed in process C according to the invention in amounts such that preferably 0.1 to 10 mol, particularly preferably 0.2 to 5 mol, of silyl groups, in each case per mole of chlorine of the organosilicon compound containing chlorine radicals employed according to the invention, are present.

The reaction according to the invention is carried out at temperatures of preferably 0 to 200° C., particularly preferably 20 to 180° C., in particular 30 to 160° C.

Process C according to the invention is preferably carried out between a pressure of 1 mbar and the pressure of the surrounding atmosphere, that is to say between 900 and 1100 hPa, depending on the reaction temperature and the organosilicon compounds containing chlorine radicals used, or the silylated ureas or urea derivatives employed.

The components employed in process C according to the invention can in each case be an individual type of such a component or at least two different types of such components. The organosilicon compound containing chlorine radicals employed according to the invention is preferably a mixture of different types.

Process A according to the invention has the advantage that it is easy to carry out and the preparation of the organosilicon compounds according to the invention takes place directly and without isolation of intermediate stages, and is thus favorable in terms of time and cost.

Process B according to the invention has the advantage that absolutely chlorine-free end products are obtained by this route.

Process C according to the invention has the advantage that it is easy to carry out and no expensive removal of ammonium salts from the product according to the invention takes place.

The organosilicon compounds according to the invention have the advantage that they can remove protic compounds, such as, for example, water, alcohols or silanols, permanently and quantitatively by chemical reaction, which as a rule leads to non-volatile and toxicologically and ecologically acceptable reaction products, such as, for example, urea or urea derivatives and sil(ox)anes.

The organosilicon compounds according to the invention or prepared according to the invention can be employed for the most diverse applications in which the object is to remove protic compounds or groups. The compounds according to the invention are particularly suitable for removal of substances with OH groups.

Examples of compounds or groups which can be removed with the organosilicon compounds according to the invention or prepared according to the invention are water, alcohols, organic acids, such as, for example, carboxylic and sulfonic acids, compounds containing silanol groups and inorganic acids with OH groups, such as, for example, sulfuric, sulfonic or nitric acids.

The amount of compounds according to the invention used here depends on the amount of protic compounds or groups to be reacted. For complete removal, preferably at least one chemical bond between silicon atom and urea unit is necessary in the compounds according to the invention per protic group to be removed.

The compounds according to the invention are especially suitable as an additive to organopolysiloxane compositions, such as, for example, RTV-1-alkoxysilicone compositions, to increase the storage stability.

The present invention also relates to organopolysiloxane compositions which can be stored with exclusion of moisture and on access of moisture can be crosslinked at room temperature to give elastomers, alcohols being split off, and which are based on (A) polydiorganosiloxanes having at least two organyloxy radicals on each end group, if appropriate (B) organyloxyfunctional crosslinking agents having at least three organyloxy groups and, if appropriate, (C) condensation catalysts, which comprise at least one (D) organosilicon compound according to the invention having at least three silicon atoms, of units of the formula (I).

The compositions according to the invention can be dimensionally stable or free-flowing, depending on the use.

The polydiorganosiloxanes employed according to the invention which have at least two organyloxy radicals on each end group are preferably those of the general formula

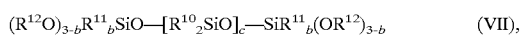

$$(R^{12}O)_{3-b}R^{11}{}_b SiO\text{—}[R^{10}{}_2 SiO]_c\text{—}SiR^{11}{}_b(OR^{12})_{3-b} \quad (VII),$$

in which b is 0 or 1, $R^{10}$ is identical or different SiC-bonded hydrocarbon radicals having 1 to 18 carbon atoms, which are optionally substituted by halogen atoms, amino groups, ether groups, ester groups, epoxy groups, mercapto groups, cyano groups or (poly)glycol radicals, the latter being built up from oxyethylene and/or oxypropylene units, and $R^{11}$ can be identical or different and has a meaning given for R, $R^{12}$ can be identical or different and is a hydrocarbon radical which has 1 to 18 carbon atoms, can be interrupted by oxygen atoms and is optionally substituted by amino, ester, ether, keto or halogen groups, and c is an integer from 10 to 10,000, preferably 100 to 3000, particularly preferably 400 to 2000.

Examples of radicals $R^{10}$ and $R^{11}$ are the examples given above for the radical R.

The radicals given above as preferred for the radical R are preferred as the radical $R^{10}$.

The radical $R^{11}$ is preferably a hydrogen atom, unsubstituted hydrocarbon radicals having 1 to 10 carbon atoms and hydrocarbon radicals having 1 to 10 carbon atoms which are substituted by amino, mercapto, morpholino, glycidoxy, acryloxy or methacryloxy groups.

The radical $R^{11}$ is particularly preferably alkyl radicals and alkenyl radicals having 1 to 4 carbon atoms, in particular the methyl, ethyl and the vinyl radical, and optionally substituted amino and glycidoxy groups bonded to the silicon atom via alkylene radicals having 2 to 6 carbon atoms.

The radical $R^{12}$ is preferably alkyl radicals having 1 to 8 carbon atoms, which can be substituted by methoxy or ethoxy groups, methyl or ethyl radicals being particularly preferred.

Examples of alkyl radicals $R^{12}$ are the examples of alkyl radicals given above for R.

The average value of the number c in formula (VII) is preferably chosen such that the organopolysiloxane of the formula (VII) has a viscosity of 1000 to 1,000,000 mm²/s, particularly preferably 5000 to 500,000 mm²/s, in each case measured at a temperature of 25° C.

Although it is not shown in formula (VII) and cannot be deduced from the term polydiorganosiloxane, up to 10 mol % of the diorganosiloxane units can be replaced by other siloxane units, which are usually present, however, only as impurities which are more or less difficult to avoid, such as $R^{10}{}_3 SiO_{1/2}$, $R^{10}SiO_{3/2}$ and $SiO_{4/2}$ units, in which $R^{10}$ has the meaning given above for this.

Examples of the polydiorganosiloxanes which have at least two organyloxy radicals on each end group (A) and are employed in the compositions according to the invention are $(MeO)_2 MeSiO[SiMe_2O]_{200-2000}SiMe(OMe)_2$,
$(EtO)_2 MeSiO[SiMe_2O]_{200-2000}SiMe(OEt)_2$,
$(MeO)_2 ViSiO[SiMe_2O]_{200-2000}SiVi(OMe)_2$,
$(EtO)_2 ViSiO[SiMe_2O]_{200-2000}SiVi(OEt)_2$,
$(MeO)_2 CapSiO[SiMe_2O]_{200-2000}SiCap(OMe)_2$,
$(MeO)_2 BapSiO[SiMe_2O]_{200-2000}SiBap(OMe)_2$ and
$(EtO)_2 BapSiO[SiMe_2O]_{200-2000}SiBap(OEt)_2$, where Me is the methyl radical, Et is the ethyl radical, Vi is the vinyl radical, Cap is the 3-(cyclohexylamino)-propyl radical and Bap is the 3-(n-butylamino)propyl radical.

The polydiorganosiloxanes which have at least two organyloxy radicals on each end group and are employed in the compositions according to the invention are commercially available products or can be prepared by processes known in silicon chemistry, for example by reaction of α,ω-dihydroxypolyorganosiloxanes with the corresponding organyloxysilanes.

The organyloxy-functional crosslinking agents (B) employed if appropriate can be any desired organyloxy crosslinking agents known to date, such as, for example, silanes or siloxanes having at least three organyloxy groups and cyclic silanes according to DE-A 36 24 206 (Wacker-Chemie GmbH; published on Feb. 11, 1988) and the corresponding U.S. Pat. No. 4,801,673, of the formula

$$(R^{14}O)_2Si\text{—}N\text{—}R^{13}, \quad (VIII)$$
$$\hspace{2.5cm}|$$
$$\hspace{2.5cm}R^{15}$$

in which $R^{13}$ is a divalent hydrocarbon radical, $R^{14}$ can be identical or different and has a meaning given for $R^{12}$ and $R^{15}$ is a hydrogen atom or an alkyl or an aminoalkyl radical.

The organyloxy crosslinking agents (B) employed, if appropriate, in the compositions according to the invention are preferably organosilicon compounds of the formula

$$(R^{12}O)_{4-d}SiR^{16}{}_d \quad (IX),$$

in which $R^{12}$ can be identical or different and has one of the meanings given above, $R^{16}$ has a meaning given above for $R^{11}$ or is a hydrocarbon radical substituted by the radical —$SiR^{11}{}_e(OR^{12})_{3-e}$, where $R^{11}$ and $R^{12}$ have the abovementioned meaning and e is 0, 1, 2 or 3 and d is 0 or 1, and partial hydrolysates thereof.

The partial hydrolysates here can be partial homohydrolysates, i.e. partial hydrolysates of one type of organosilicon compound of the formula (IX), and also partial cohydrolysates, i.e. partial hydrolysates of at least two different types of organosilicon compounds of the formula (IX).

If the crosslinking agents (B) employed, if appropriate, in the compositions according to the invention, are partial hydrolysates of organosilicon compounds of the formula (IX), those having up to 6 silicon atoms are preferred.

Examples of the radical $R^{16}$ are the examples mentioned above for the radical $R^{11}$, and hydrocarbon radicals having 1 to 6 carbon atoms which are substituted by radicals —$SiR^1_e(OR^{12})_{3-e}$ in which e is 0 or 1 and $R^{12}$ has the abovementioned meaning.

Preferred radicals $R^{16}$ are the radicals mentioned as preferred for $R^{11}$ and hydrocarbon radicals having 1 to 6 carbon atoms which are substituted by radicals —$SR^{11}_e(OR^{12})_{3-e}$, in which e is 0 or 1 and $R^{12}$ has the abovementioned meaning.

Particularly preferred radicals $R^{16}$ are the radicals mentioned as particularly preferred for $R^{11}$ and hydrocarbon radicals having 2 carbon atoms which are substituted by radicals —$Si(Or^{12})_3$, in which $R^{12}$ is the ethyl or methyl radical.

The crosslinking agents (B) employed, if appropriate, in the compositions according to the invention are particularly preferably tetramethoxysilane, tetraethoxysilane, tetrapropoxysilane, tetrabutoxysilane, methyltrimethoxysilane, methyltriethoxysilane, vinyltrimethoxysilane, vinyltriethoxysilane, phenyltrimethoxysilane, phenyltriethoxysilane, 3-aminopropyltrimethoxysilane, 3-aminopropyltriethoxysilane, 3-cyanopropyltrimethoxysilane, 3-cyanopropyltriethoxysilane, 3-(2-aminoethylamino)propyltrimethoxysilane, 3-(2-aminoethylamino)propyltriethoxysilane, 3-(N,N-diethyl-2-aminoethylamino)propyltrimethoxysilane, 3-(N,N-diethyl-2-aminoethylamino)propyltriethoxysilane, 3-(cyclohexylamino)propyltrimethoxysilane, 3-(cyclohexylamino)propyltriethoxysilane, 3-(glycidoxy)propyltriethoxysilane, 1,2-bis(trimethoxysilyl)ethane, 1,2-bis-(triethoxysilyl)ethane and partial hydrolysates of the alkoxy-functional organosilicon compounds mentioned, such as, for example, hexaethoxydisiloxane.

The crosslinking agents (B) employed in the compositions according to the invention are commercially available products or can be prepared by processes known in silicon chemistry.

The compositions according to the invention comprise crosslinking agents (B) in amounts of preferably 0 to 50 parts by weight, particularly preferably 0.1 to 20 parts by weight, in particular 0.5 to 10 parts by weight, in each case per 100 parts by weight of organopolysiloxane (A).

The compositions according to the invention can comprise any desired condensation catalysts (C), which have also been able to be present to date in compositions which can be stored with exclusion of water and on access of water crosslinked to give elastomers at room temperature. These include all the condensation catalysts mentioned in the abovementioned DE-A 38 01 389, such as, for example, butyl titanates and organic tin compounds, such as di-n-butyltin diacetate, di-n-butyltin dilaurate and reaction products of a silane containing, as hydrolyzable groups, at least two monovalent hydrocarbon radicals per molecule which are bonded to silicon via oxygen and are optionally substituted by an alkoxy group, or an oligomer thereof, with a diorganotin diacylate, it being possible for all the valencies of the tin atoms in these reaction products to be satisfied by oxygen atoms of the grouping

or by SnC-bonded, monovalent organic radicals.

Preferred condensation catalysts (C) are organometallic condensation catalysts, in particular derivatives of titanium, aluminum, tin and calcium and zinc, dialkyltin compounds and zinc dicarboxylates being particularly preferred.

Examples of preferred organometallic condensation catalysts are the dialkyl di(β-diketo)stannates, dialkyltin dicarboxylates, calcium and zinc dicarboxylates and butyltitanium chelate compounds described in U.S. Pat. No. 4,517,337 (General Electric Co; published on May 14, 1985).

Examples of particularly preferred organometallic condensation catalysts are dibutyltin diacetate, dibutyltin dilaurate, dibutyltin di(2-ethylhexanoate) and zinc di(2-ethylhexanoate).

The compositions according to the invention comprise condensation catalysts (C) in amounts of preferably 0 to 10 parts by weight, particularly preferably 0.01 to 5 parts by weight, in particular 0.1 to 4 parts by weight, in each case per 100 parts by weight of organopolysiloxane (A).

Examples of component (D) employed in the compositions according to the invention are those above for the organosilicon compounds according to the invention of units of the formula (I).

Component (D) employed according to the invention is preferably one of units of the formula (I) where r is 0, organosilicon compounds according to the invention of units of the formula (I) where r=m=0 being particularly preferably employed.

The compositions according to the invention comprise compound (D) in amounts of preferably 0.1 to 30 parts by weight, particularly preferably 0.5 to 20 parts by weight, in particular 0.5 to 10 parts by weight, in each case per 100 parts by weight of organopolysiloxane (A).

In addition to components (A), (B), (C) and (D) described above, the compositions according to the invention can now comprise further substances, such as plasticizers (E), fillers (F), adhesion promoters (G) and additives (H), it being possible for the additional substances (E) to (H) to be the same as have also been employed to date in compositions which can be crosslinked, alcohols being split off.

Examples of plasticizers (E) are dimethylpolysiloxanes which are blocked on the ends by trimethylsiloxy groups and are liquid at room temperature, and high-boiling hydrocarbons, such as, for example, paraffin oils.

The compositions according to the invention comprise plasticizers (E) in amounts of preferably 0 to 300 parts by weight, particularly preferably 10 to 200 parts by weight, in particular 20 to 100 parts by weight, in each case per 100 parts by weight of organopolysiloxane (A).

Examples of fillers (F) are non-reinforcing fillers, that is to say fillers having a BET surface area of up to 50 m$^2$/g, such as quartz, diatomaceous earth, calcium silicate, zirconium silicate, zeolites, metal oxide powders, such as aluminum, titanium, iron or zinc oxides or mixed oxides thereof, barium sulfate, calcium carbonate, gypsum, silicon nitride, silicon carbide, boron nitride and powders of glass and plastic, such as polyacrylonitrile powder; reinforcing fillers, that is to say fillers having a BET surface area of more than 50 m$^2$/g, such as pyrogenically prepared silicic acid, precipitated silicic acid, precipitated chalk, carbon black, such as furnace and acetylene black, and silicon/aluminum mixed oxides of high BET surface area; and fibrous fillers, such as asbestos and synthetic fibers. The fillers mentioned can be hydrophobized, for example by treatment with organosilanes or -siloxanes or with stearic acid or by etherification of hydroxyl groups to alkoxy groups.

The compositions according to the invention comprise fillers (F) in amounts of preferably 0 to 300 parts by weight, particularly preferably 1 to 200 parts by weight, in particular 5 to 200 parts by weight, in each case per 100 parts by weight of organopolysiloxane (A).

Examples of the adhesion promoters (G) employed in the organopolysiloxane compositions according to the invention are silanes and organopolysiloxanes having functional groups, such as, for example, those with aminoalkyl, glycidoxypropyl or methacryloxypropyl radicals, as well as tetraalkoxysilanes. However, if another component already has the functional groups mentioned, such as, for example, siloxane (A) or crosslinking agent (B), an addition of an adhesion promoter can be omitted.

The compositions according to the invention comprise adhesion promoters (G) in amounts of preferably 0 to 50 parts by weight, particularly preferably 1 to 20 parts by weight, in particular 1 to 10 parts by weight, in each case per 100 parts by weight of organopolysiloxane (A).

Examples of additives (H) are pigments, dye-stuffs, odoriferous substances, fungicides, oxidation inhibitors, agents for influencing the electrical properties, such as conductive carbon black, agents which render the compositions flame-retardant, light stabilizers and agents for prolonging the skin formation time, such as silanes having an SiC-bonded mercaptoalkyl radical, cell-generating agents, for example azodicarboxamide, heat stabilizers and thixotropic agents, such as, for example, phosphoric acid esters according to DE-A 26 53 499.

The compositions according to the invention comprise additives (H) in amounts of preferably 0 to 100 parts by weight, particularly preferably 0 to 30 parts by weight, in particular 0 to 10 parts by weight, in each case per 100 parts by weight of organopolysiloxane (A).

The compositions according to the invention are preferably those which comprise
(A) polydiorganosiloxane of the formula (VII),
(B) crosslinking agent,
(C) condensation catalyst,
(D) one or more of the organosilicon compounds according to the invention having at least 3 silicon atoms, of units of the formula (I) and
if appropriate further substances.

The compositions according to the invention are particularly preferably those which consist of
(A) 100 parts by weight of polydiorganosiloxane of the formula (VII),
(B) 0.1 to 50 parts by weight of crosslinking agent of the formula (IX),
(C) 0.01 to 10 parts by weight of organometallic condensation catalyst,
(D) 0.1 to 30 parts by weight of the organosilicon compounds according to the invention having at least 3 silicon atoms, of units of the formula (I),
(E) 0 to 300 parts by weight of plasticizer,
(F) 0 to 300 parts by weight of fillers,
(G) 0 to 50 parts by weight of adhesion promoter and
(H) 0 to 100 parts by weight of additives.

The individual components of the compositions according to the invention can in each case be one type of such a component or else a mixture of at least two different types of such components.

To prepare the compositions according to the invention, all the constituents of the particular composition can be mixed with one another in any desired sequence. This mixing can be carried out at room temperature under the pressure of the surrounding atmosphere, that is to say about 900 to 1100 hPa. If desired, however, this mixing can also be carried out at higher temperatures, for example at temperatures in the range from 35° C. to 135° C.

The preparation of the organopolysiloxane compositions according to the invention and storage thereof must take place under essentially anhydrous conditions, since otherwise the compositions may cure prematurely.

The usual water content of air is adequate for crosslinking the compositions according to the invention to give elastomers. If desired, the crosslinking can also be carried out at temperatures higher or lower than room temperature, for example at −5° to 10° C. or at 30° to 50° C.

The present invention furthermore relates to shaped articles produced by crosslinking the compositions according to the invention.

The organopolysiloxane compositions according to the invention which can be crosslinked to give elastomers, alcohols being split off, have the advantage that they are distinguished by a very high storage stability and a high rate of crosslinking. The compositions according to the invention thus show constant vulcanization properties at any point in time during storage for at least 18 months at room temperature.

The compositions according to the invention furthermore have the advantage that the organosilicon compounds according to the invention having at least 3 silicon atoms, of units of the formula (I), already react with OH groups, in particular with alcohol and/or water and/or Si-OH groups, at room temperature. Compounds having OH groups here in RTV alkoxy compositions are chiefly water, which is entrained into the composition with the constituents of the recipe, such as, for example, the polysiloxane or the fillers, alcohols, which are formed during blocking of the ends of the OH-polymers and the reaction of Si—OH groups or water with the crosslinking agent, and Si—OH groups on polysiloxanes and above all on the silicic acid employed, if appropriate, as a filler. During these reactions, advantageously no volatile cleavage products which are ecologically unacceptable or are an odor nuisance are liberated.

The compositions according to the invention or prepared according to the invention can be employed for all intended uses for which organopolysiloxane compositions which can be stored with exclusion of water and on access of water crosslink to form elastomers at room temperature can be employed.

The compositions according to the invention or prepared according to the invention are thus excellently suitable, for example, as sealing compositions for joints, including vertically running joints, and similar empty spaces of, for example, 10 to 40 mm internal diameter, for example in buildings, landcraft, watercraft and aircraft, or as adhesives or cementing compositions, for example in window construction or in the production of aquaria or showcases, and, for example, for the production of protective coverings, including those for surfaces exposed to the constant action of fresh water or sea water, for coverings which prevent sliding, or rubber-elastic shaped articles, and for insulation of electrical or electronic devices.

In the examples described below, all the viscosity data are based on a temperature of 25° C. Unless stated otherwise, the examples below are carried out under a pressure of the surrounding atmosphere, that is to say under about 1000 hPa, and at room temperature, that is to say at about 23° C., or at a temperature which is established when the reactants are brought together at room temperature without additional heating or cooling, and at a relative atmospheric humidity of about 50%. All parts and percentages data furthermore relate to the weight, unless stated otherwise.

In the following examples, the Shore A hardness is determined in accordance with DIN 53 505-87/Standard bar S1 (German Industrial Standard). The following abbreviations are furthermore used in the Examples: Me is the methyl radical.

EXAMPLE 1

A mixture of 8.8 g of trimethylchlorosilane (0.08 mol) and 20.3 g of trichlorotetramethyldisiloxane (0.1 mol) is added dropwise to a suspension of 10.15 g of urea (0.17 mol), 17.12 g of triethylamine (0.17 mol) and 67 g of tetrahydrofuran in the course of 90 minutes such that the temperature of the reaction mixture remains below 30° C. After heating at 50° C. for 10 minutes, the precipitate formed is filtered off. The precipitate is rinsed with 300 ml of tetrahydrofuran, the filtrates are combined and the solvent is then stripped off. The resulting residue is viscous at 90° C., and is solid at room temperature. With the aid of the $^1$H- and $^{29}$Si-NMR spectrum, the average composition of the product results as $[Me_3Si(NH—C=O—NH)_{1/2}]_2[Me_2SiO_{1/2}(NH—C=O—NH)_{1/2}]_{16}[Me_2SiO_{2/2}]_9$.

EXAMPLE 2

Gaseous ammonia is passed into a mixture of 400 ml of anhydrous toluene and 330 g (about 1 mol) of an organosilicon compound containing chlorine radicals, of the average formula $Me_3Si(OMe_2Si)_3Cl$, until the reaction mixture gives a basic reaction. Thereafter, the ammonium chloride obtained as a by-product during the reaction is filtered off and the residue is rinsed with two portions of 50 ml of anhydrous toluene. The toluene is distilled off from the combined toluene solutions. 200 g of a clear liquid remain, which, according to $^{29}$Si-NMR, is a mixture of siloxanylamines and corresponds to an average formula of $(Me_3Si(OMe_2Si)_3)_2NH$.

A mixture of 170 g of the siloxanylamine prepared above, of the average formula $[Me_3Si(OMe_2Si)_3]_2NH$, 0.3 g of ammonium sulfate and 15 g of urea is heated at 140° C. until the evolution of ammonia to be observed comes to an end.

Excess siloxanylamine is then stripped off. The resulting residue is viscous at room temperature, with a viscosity of about 9000 mm$^2$/s.

With the aid of the $^1$H- and $^{29}$Si-NMR spectrum, the average composition of the product results as $[Me_3SiO_{1/2}]_5[Me_2SiO_{1/2}(NH—C=O—NH)_{1/2}]_2[Me_2SiO_{2/2}]_4$.

EXAMPLE 3

51 g of N,N'-bis(trimethylsilyl)urea and 130 g of a mixture of 3% dichlorodecamethylpentasiloxane, 64% dichlorododecamethylhexasiloxane, 31% dichlorotetradecamethylheptasiloxane and 2% dichlorohexadecamethyloctasiloxane are stirred at a temperature of 80° C. for about 1 hour, the pressure of 500 mbar initially applied being reduced to finally about 1 mbar in the course of the reaction, as a result of which by-products of the reaction are removed. The resulting residue is viscous at room temperature. With the aid of the $^1$H- and $^{29}$Si-NMR spectrum, the average composition of the product results as $[Me_3Si(NH—C=O—NH)_{1/2}][Me_2SiO_{1/2}(NH—C=O—NH)_{1/2}]_{65}[Me_2SiO_{2/2}]_{338}$. The distillate contains the reaction by-products trimethylchlorosilane and hexamethyldisiloxane in a molar ratio of 13:1.

EXAMPLE 4

An RTV-1-silicone sealing composition is prepared. For this, 48.75 g of α,ω-bis(dimethoxymethylsiloxy)polydimethylsiloxane of viscosity 1000 mm$^2$/s, 32 g of α,ω-bis(trimethylsiloxy)polydimethyldisiloxane of viscosity 100 mm$^2$/s, 2 g of methyltrimethoxysilane, 4.5 g of 3-aminopropyltriethoxysilane and 9.5 g of the organosilicon compound containing urea radicals prepared in Example 3 are mixed. 9 g of pyrogenic silicic acid having a specific surface area, measured by the BET method, of 150 m$^2$/g are then incorporated homogeneously into the composition, and 0.25 g of dibutyltin diacetate is mixed in. Finally, the mixture is stirred under a pressure of 10–20 mbar in order to remove the air included during mixing.

Tubes are filled air-tight with the composition thus prepared and are stored at 50° C. Immediately after preparation and after storage for 2, 4, 8 and 12 weeks, the skin formation time is determined with the aid of worms (time taken for a dry surface to form on the worm) and the Shore A hardness is determined with the aid of films 2 mm thick.

The results are summarized in Table 1.

COMPARISON EXAMPLE 1

The procedure described in Example 4 is repeated, with the modification that no organosilicon compound containing urea radicals is employed.

The results are summarized in Table 1.

EXAMPLE 5

The procedure described in Example 4 is repeated, with the modification that instead of 9.5 g of the organosilicon compound containing urea radicals prepared in Example 3, 6.3 g of the organosilicon compound containing urea radicals prepared in Example 2 are employed. The results are summarized in Table 1.

EXAMPLE 6

The procedure described in Example 4 is repeated, with the modification that instead of 9.5 g of the organosilicon compound containing urea radicals prepared in Example 3, 2.8 g of the organosilicon compound containing urea radicals prepared in Example 1 are employed. The results are summarized in Table 1.

| Example | after preparation SFT | Shore A | after 2 weeks SFT | Shore A | after 4 weeks SFT | Shore A | after 8 weeks SFT | Shore A | after 12 weeks SFT | Shore A |
|---|---|---|---|---|---|---|---|---|---|---|
| 4 | 9 min | 20–25 | 5 min | 22–23 | 6 min | 23–24 | 6 min | 20–25 | 4 min | 19–22 |
| V1 | 5 min | 25–27 | >24 h | n.m. | n.c. | n.m. | n.c. | n.m. | n.c. | n.m. |

-continued

| | after preparation | | after 2 weeks | | after 4 weeks | | after 8 weeks | | after 12 weeks | |
|---|---|---|---|---|---|---|---|---|---|---|
| Example | SFT | Shore A | SFT | Shore A | SFT | Shore A | SFT | Shore A | SFT | Shore A |
| 5 | 12–17 min | 20 | <6 min | 20–25 | 3–6 min | 20 | 5 min | 18–22 | 4–5 min | 20 |
| 6 | 40–45 min | 10–15 | 50–60 min | 9–12 | 45–50 min | 11–14 | 45–55 min | 10–13 | 40–50 min | 11–15 |

Legend:
SFT = skin formation time
n.c. = no crosslinking after storage in air for 7 days
n.m. = not measurable;
min = minutes;
h = hours

EXAMPLE 7

A dish with 5 g of water is placed in a desiccator under normal pressure at room temperature. A second dish with 100 g of the organosilicon compound containing urea radicals prepared in Example 1 is added. The change in atmospheric humidity, i.e. the water content of the atmosphere, in the desiccator is then monitored. The atmospheric humidity decreases from initially 65% to
35% after 1 day,
18% after 2 days,
5% after 5 days and
0% after 10 days.
The organosilicon compound containing urea radicals is converted here into urea and polydimethylsiloxane.

EXAMPLE 8

Example 7 is repeated, with the modification that instead of 5 g of water, 5 g of methanol are used. After 10 days, methanol is no longer detectable in the atmosphere.

The organosilicon compound containing urea radicals is converted here into urea, trimethylmethoxysilane and homologs of the series MeO—(SiMe$_2$O)$_n$SiMe$_2$—OMe where n=0, 1, 2, 3, 4, 5, 6 or 7.

What is claimed is:

1. An organosilicon compound containing at least three silicon atoms, comprising units of the formula

    (I)

where Y is

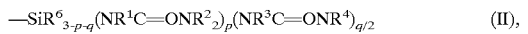    (II), in which R, R$^1$, R$^2$, R$^3$, R$^4$, R$^5$ and R$^6$ independently of one another can in each case be identical or different and are a hydrogen atom or optionally substituted monovalent hydrocarbon radicals having 1 to 20 carbon atoms, a is 0, 1, 2 or 3,
k is 0, 1, 2 or 3,
t is 0, 1, 2, 3 or 4,
n is 0, 1, 2, 3 or 4,
m is 0 or 1,
r is 0 or 1,
s is an integer from 1 to 20,
p is 0, 1, 2 or 3 and
q is 0, 1, 2 or 3, with the proviso that
the sum p+q is ≦3,
the sum a+k+t+m+n+r is 4,
the sum m+r is 0 or 1, and
wherein the organosilicon compound according to the invention contains at least one unit of the formula (I) where t is other than 0.

2. An organosilicon compound as claimed in claim 1, wherein r is 0.

3. An organosilicon compound as claimed in claim 1, wherein r is 0 and m is 0.

4. A process for the preparation of an organosilicon compound as claimed in claim 1 comprising reacting urea (derivatives) of the formula

    (III)

in which R$^7$ and R$^8$ can be identical or different and have the meanings given above for R$^1$, R$^2$, R$^3$ and R$^4$, with the proviso that at least one compound of the formula (III) having at least one radical R$^8$ which is a hydrogen atom is employed;

with organosilicon compounds containing chlorine radicals comprising units of the formula

    (IV)

in which R, R$^5$, Y, a, n, m, r and s can in each case be identical or different and have the meaning given above for these symbols, and u is 0, 1, 2, 3 or 4, with the proviso that the sum a+n+m+r+u is 4 and at least one compound of units of the formula (IV) having at least one chlorine atom per molecule is present, HCl being split off.

5. A process for the preparation of an organosilicon compound as claimed in claim 1, which comprises
in a 1st step
reacting organosilicon compounds containing chlorine radicals comprising units of the formula (IV)

    (IV)

in which R, R$^5$, Y, a, n, m, r and s can in each case be identical or different and have the meaning given above for these symbols, with the proviso that the sum a+n+m+r+u is 4, and at least one compound comprising units of the formula (IV) having at least one chlorine atom per molecule is present, with amino compounds of the formula $R^9{}_2NH$ (V)

in which $R^9$ can be identical or different and has a meaning given for the radical R, and in a 2nd step reacting the organosilicon compounds obtained in the 1st step with urea (derivatives) of the formula (III),

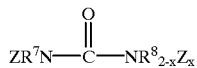  (III)

in which $R^7$ and $R^8$ can be identical or different and have the meanings given above for $R^1$, $R^2$, $R^3$ and $R^4$, with the proviso that at least one compound of the formula (III) having at least one radical $R^8$ which is a hydrogen atom is employed, optionally in the presence of catalysts.

6. A process for the preparation of an organosilicon compound as claimed in claim 2 comprising reacting silylated urea (derivatives) of the formula

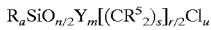  (VI)

in which $R^7$ and $R^8$ have the meanings given above for these radicals, Z is a silyl radical and x is 0 or 1, with the proviso that the compound of the formula (VI) contains not more than 2 silicon atoms and at least one compound of the formula (VI) where x=1 is employed, with organosilicon compounds containing chlorine radicals, of units of the formula (IV)

$R_aSiO_{n/2}Y_m[(CR^5{}_2)_s]_{r/2}Cl_u$ in which R, $R^5$, Y, a, n, m, r and s can in each case be identical or different and have the meaning given above for these symbols, with the proviso that the sum a+n+m+r+u is 4 and at least one compound of units of the formula (IV) having at least one chlorine atom per molecule is present.

7. In a moisture curable, one component organopolysiloxane composition, comprising:

(A) polydiorganosiloxanes having at least two organyloxy radicals on each end group, (B) optionally, organyloxyfunctional crosslinking agents having at least three organyloxy groups and, (C) optionally, condensation catalysts, the improvement comprising including in said moisture curable, one component organopolysiloxane, (D) at least one organosilicon compound as claimed in claim 1.

8. A shaped article prepared by curing the composition of claim 7.

9. A process for the elimination of protic groups in a composition, said process comprising adding to said composition an effective protic group-removing amount of the organosilicon compound of claim 1.

10. An organo silicon compound of claim 1, selected from the group consisting of $[Me_3Si(NH—C=O—NH)][SiMe_2O]_x[SiMe_2—NH—C=O—NH—]_y[SiMe_3]$
where x=0–1000, y=0–500, x+y≧1;

$[Me_3Si(OSiMe_2)_4(NH—C=O—NH)][SiMe_2O]_x[SiMe_2—NH—C=O—NH]_y[(SiMe_2O)_4SiMe_3]$
where x=0–1000, y=0–500, x+y≧21;

$[Me_3Si(NMe—C=O—NMe)][SiMe_2O]_x[SiMe_2(NMe—C=O—NMe)]_y[SiMe_3]$
where x=0–1000, y=0–500, x+y≧1;

$[Me_3Si(OSiMe_2)_4(NMe—C=O—NMe)][SiMe_2O]_x[SiMe_2(NMe—C=O—NMe)]_y[(SiMe_2O)_4SiMe_3]$
where x=0–1000, y=0–500, x+y≧1;

$[MeSi(NH—C=O—NH)_{2/2}(NH—C=O—NH_2)][MeSi(NH—C=O—NH)_{3/2}]_2$;

$[MeSi(NH—C=O—NH)_{1/2}(NH—C=O—NH_2)_2]_2$
$[MeSi(NH—C=O—NH)_{2/2}(NH—C=O—NH_2)]_3$
$[MeSi(NH—C=O—NH)_{3/2}]_{12}$;

$[MeSi(NPh—C=O—NPh)_{1/2}(NPh—C—O=NPh_2)_2]_2$
$[MeSi(NPh—C=O—NPh)_{2/2}(Nph—C=O—NPh_2)]_3$
$[MeSi(NPh—C=O—NPh)_{3/2}]_{12}$;

$[ViSi(NH—C=O—NH)_{1/2}(NH—C=O—NH_2)_2]_2[ViSi(NH—C=O—NH)_{2/2}(NH—C=O—NH_2)]_3[ViSi(NH—C=O—NH)_{3/2}]_{12}$;

$[MeSi(NH—C=O—NH)_{1/2}(NH—C=O—NH_2)_2]_2$
$[MeSi(NH—C=O—NH)_{2/2}(NH—C=O—NH_2)]_2$
$[MeSi(NH—C=O—NH)_{3/2}]_2[(NH—C=O—NH)_{1/2}(SiMe_2O)_xSiMe_2(NH—C=O—NH)_{1/2}]_y$
where x=0–20, y=0–50;

$[ViSi(NH—C=O—NH)_{1/2}(NH—C=O—NH_2)_2]_2[ViSi(NH—C=O—NH)_{2/2}(NH—C=O—NH_2)]_2$; and $[ViSi(NH—C=O—NH)_{3/2}]_2[(NH—C=O—NH)_{1/2}(SiMe_2O)_xSiMe_2(NH—C=O—NH)_{1/2}]_y$
where x=0 to 20, y =0 to 50;

where Me is methyl, Vi is vinyl, and Ph is phenyl.

11. An organo silicon compound of claim 1, selected from the group consisting of $[MeSi(NH—C=O—NH)_{2/2}\{SiMe(NH—C=O—NH)_{1/2}(NH—C=O—NH_2)\}]_7$;

$[MeSi(NH—C=O—NH)_{1/2}(NH—C=O—NH_2)\{SiMe(NH—C=O—NH)_{1/2}(NH—C=O—NH_2)\}]_4$;

$[MeSi(NH—C=O—NH)_{2/2}\{SiMe(NH—C=O—NH_2)_2\}]_3$;

$[MeSi(NH—C=O—NH)_{2/2}\{SiMe(NH—C=O—NH)_{2/2}\}]_2$;

$[MeSi(NH—C=O—NH)_{1/2}(NH—C=O—NH_2)\{SiMe(NH—C=O—NH_2)_2\}]$;

$[MeSi(NH—C=O—NH)_{2/2}\{SiMe(NH—C=O—NH)_{1/2}(NH—C—O—NH_2)\}]_3$;

$[MeSi(NH—C=O—NH)_{1/2}(NH—C=O—NH_2)\{SiMe(NH—C=O—NH)_{1/2}(NH—C=O—NH_2)\}]_6$;

$[MeSi(NH—C=O—NH)_{2/2}\{SiMe(NH—C=O—NH_2)_2\}]_4$;

$[MeSi(NH—C=O—NH)_{2/2}\{SiMe(NH—C=O—NH_{2/2})\}]_2$;

$[MeSi(NH—C=O—NH)_{1/2}(NH—C=O—NH_2)\{SiMe(NH—C=O—NH_2)_2\}]$;

$[SiMe_2(NH—C=O—NH)_{2/2}]_{20}$;

$[MeSi\{(CH_2)_2\}_{1/2}(NH—C=O—NH_2)_{1/2}(NH—C=O—NH_2)]_5$; $[MeSi\{(CH_2)_2\}_{1/2}(NH—C=O—NH)_{2/2}]_4$; $[MeSi\{(CH_2)_2\}_{1/2}(NH—C=O—NH_2)_2]$ and $[SiMe_2(NH—C=O—NH)_{2/2}]_{10}$, where Me is methyl, Vi is vinyl, and Ph is phenyl.

* * * * *

UNITED STATES PATENT AND TRADEMARK OFFICE
CERTIFICATE OF CORRECTION

PATENT NO. : 6,218,498 B1　　　　　　　　　　　　　　　　　　　Page 1 of 1
DATED : April 17, 2001
INVENTOR(S) : Stefan Oberneder, et al It is certified that error appears in the above-identified patent and that said Letters Patent is hereby corrected as shown below:

Column 22, claim 10:
Line 3, delete "$x+y \geq 21$" and insert -- $x+y \geq 1$ -- .

Signed and Sealed this

Eleventh Day of September, 2001

Attest:

NICHOLAS P. GODICI
*Attesting Officer*　　　*Acting Director of the United States Patent and Trademark Office*